United States Patent [19]
Humphrey et al.

[11] Patent Number: 5,674,745
[45] Date of Patent: Oct. 7, 1997

[54] BIOTRANSFORMATION OF FATTY SUBSTRATES

[75] Inventors: Anthony Martin Humphrey, Chorleywood; Bridget Ann Skill, Leigh-On-Sea; Judith L. Kinderlerer, Sheffield, all of England

[73] Assignee: Bush Boake Allen Limited, London, England

[21] Appl. No.: 455,318

[22] Filed: May 31, 1995

Related U.S. Application Data

[62] Division of Ser. No. 896,705, Jun. 10, 1992, which is a division of Ser. No. 576,633, Aug. 31, 1990, Pat. No. 5,185,282, which is a division of Ser. No. 510,488, Apr. 18, 1990, abandoned.

[30] Foreign Application Priority Data

Aug. 31, 1989 [GB] United Kingdom .................... 8919671

[51] Int. Cl.[6] ........................................... C12M 3/00
[52] U.S. Cl. ........................ 435/299.1; 422/211; 422/212; 422/220
[58] Field of Search ........................ 435/299.1, 291.1; 422/211, 212, 220

[56] References Cited

U.S. PATENT DOCUMENTS

| 683,362 | 9/1901 | Weisenfeld | 435/291.1 |
|---|---|---|---|
| 3,100,153 | 8/1963 | Knight | 99/116 |
| 3,720,520 | 3/1973 | Luksas | 99/140 R |
| 4,029,546 | 6/1977 | Brouillard | 435/94 |
| 4,033,820 | 7/1977 | Brouillard | 435/94 |
| 4,065,580 | 12/1977 | Feldman et al. | 426/33 |
| 4,212,949 | 7/1980 | Kozhemyakin et al. | 435/315 |
| 4,451,566 | 5/1984 | Spencer | 435/162 |
| 4,769,243 | 9/1988 | Kanisawa et al. | 426/33 |
| 4,814,117 | 3/1989 | Leva | 261/94 |
| 4,832,965 | 5/1989 | Pratt | 426/33 |
| 4,957,862 | 9/1990 | Creuly et al. | 435/148 |
| 5,010,004 | 4/1991 | Kosugi et al. | 435/134 |
| 5,061,498 | 10/1991 | Matsuzaki et al. | 426/33 |
| 5,326,550 | 7/1994 | Adris et al. | 423/652 |

OTHER PUBLICATIONS

Aidoo, K.E. et al., "Solid Substrate Fermentations", in Advances in Applied Microbiology, Laskin, A., ed., Academic Press, New York, 1982, pp. 201–237.

Jolly, R. and Kosikowski, "Blue Cheese Flavor by Microbial Lipases and Mold Spores Utilizing Whey Powder, Butter and Coconut Fats", *J. of Food Science* 1975, 40, 285–287.

Kinderlerer, J., "Conversion of Coconut Oil to Methyl Ketones by Two Asperigillus Species", *Phytochemistry* 1987 26(5), 1417–1420.

Kinderlerer, J. and Kellard, "Ketonic Rancidity in Coconut Due to Xerophilic Fungi", *Phytochemistry* 1984, 23(12), 2847–2849.

Meyrath, J., "Fungal Amylase Production", *Process Biochemistry* Jul. 1966, 234–238.

Oriol, E. et al., "Solid–State Culture of *Aspergillus niger* on Support", *J. Ferment. Technol.* 1988, 66(1), 57–62.

*Primary Examiner*—David A. Redding
*Attorney, Agent, or Firm*—Woodcock Washburn Kurtz Mackiewicz & Norris LLP

[57] ABSTRACT

This invention relates to a process for enzymic oxidation of a fatty acid to produce an oxidation product in the presence of water and oxygen wherein the fatty acid, water and enzyme for the oxidation are substantially uniformly distributed throughout a porous bed of solid support material in the substantial absence of a continuous liquid phase, oxygen is passed through the porous bed and the oxidation product is recovered from the porous bed. The invention is of particular value for production of methyl ketones from saturated fatty acids.

Apparatus for carrying out the process is also novel and includes a sealable vessel that can contain a porous bed of solid support material, a gas inlet for supplying oxygenating gas to the reactor, a gas outlet, passage means defining a plurality of upwardly extending passages that can open along their length into the bed and that communicate with the inlet and that are preferably spaced 5 to 20 cm (preferably 5 to 15 cm) apart, and means for forcing oxygenating gas through the inlet and along and out from the passages and into the bed.

4 Claims, 4 Drawing Sheets

BIOTRANSFORMATION OF FATTY SUBSTRATES

This is a division of application Ser. No. 07/896,705, filed Jun. 10, 1992, which is a divisional application of U.S. Ser. No. 07/576,633 filed on Aug. 31, 1990, now U.S. Pat. No. 5,185,282 which is a divisional application of U.S. Ser. No. 07/510,488 filed Apr. 18, 1990, now abandoned; which claims foreign priority under 35 U.S.C. §119 from British Application No. 8919671.1 filed Aug. 31, 1989.

This invention relates to a process for aerobic enzymic reactions for oxidation of fatty substrates that can be carried out in relatively high concentrations and can permit the recovery of high yields of desired product.

BACKGROUND OF THE INVENTION

Enzymic hydrolyses and oxidation processes occur naturally both in solid and liquid media, and generally give a range of products. The crude mixture may be unpleasant, but individual components may be desirable. Therefore, it is known to perform the processes artificially for oxidation of naturally occurring materials.

Commercial aerobic enzymic processes are normally carried out in solution. This has to be relatively dilute to allow oxygen to be distributed easily throughout the mixture, as otherwise aeration becomes difficult. Thus, the biotransformation solution must be a dilute solution and the yields resulting from such a dilute solution are relatively low.

Solid state processes are also known. The solid phase can be the substrate that is to be converted (e.g., malting of barley grains) or can be a support for the aqueous medium in which the oxidation occurs. In *Process Biochemistry*, July 1966, J. Meyrath describes production of amylolytic enzymes by growth of various molds which produce such enzymes on bran and on vermiculite to obtain a yield of the amylase enzyme. In addition, Oriol et al., in the *Journal of Fermentation Technology*, volume 66, number 1, pages 57 to 62, describe how *Aspergillus niger* fungus was grown on a solid support of sugar cane bagasse.

The solid state process described by Meyrath is for the production of the enzyme itself. However, it is also known to use the enzymes formed to obtain the biotransformation products that they produce. Another solid state reaction is discussed in *Advances in Applied Microbiology*, volume 28, pages 201 to 237, for the production of citric acid on inert materials. Sawdust and sugar-free sugar cane bagasse were used as the growth support, and this was impregnated with sugar solution. The inert materials were inoculated with mold culture, and citric acid was produced. Other growth supports mentioned are rice hulls and wheat bran.

It is known that natural atmospheric oxidation of fats and oils produces a crude, unpleasant product (e.g., rancidity), but that some components of the product can be useful.

In *Phytochemistry* (1984) volume 23, number 12, pages 2847 to 2849, Kinderlerer describes natural oxidation of coconut due to the action of molds natural to the coconut as giving a series of aliphatic methyl ketones and secondary alcohols. In *Phytochemistry* (1987) volume 26, number 5, pages 1417 to 1420, she described their production in a liquid medium, following growth of *Aspergillus ruber* and *A. repens* fungi with coconut oil as the sole carbon source. However, low yields were obtained.

It is also known to use milk and milk compounds as a growth medium for biotransformation reactions. For example, ketones have been produced by biotransformation processes on milk and milk compounds. In U.S. Pat. No. 3,100,153, a process is described wherein pasteurized homogenized milk containing milk fat is fermented under submerged aerobic conditions using *Penicillium roqueforti* to produce ketones, and in U.S. Pat. No. 3,720,520, ketones giving a blue cheese flavor are produced by growing *Penicillium roqueforti* with aeration in an aqueous medium of sodium caseinate and fat.

Such blue cheese flavors are also described in pages 285-287 of volume 40 (1975) of the *Journal of Food Science*, where R. Jolly and F. V. Kosikowski report studies of biotransformation of coconut fat and butter fat with whey powder, carried out in an aqueous medium, again using *Penicillium roqueforti*.

U.S. Pat. No. 4,769,243 describes the preparation of green aroma compounds by reaction of at least one unsaturated fatty acid (which may be produced in situ from fat and lipase) with enzymes from soy beans. An aqueous solution of water and ground germinating soy beans is mixed with linseed oil, and the mixture is allowed to react while stirring rapidly. Air or oxygen is supplied to the mixture throughout the reaction. The resulting reaction is due to the enzymes present in the germinating soy bean. This type of liquid process must be stirred rapidly to ensure that the mixture remains substantially homogeneous. In addition, it is difficult to provide oxygen throughout the whole reaction mixture, and so liquid mixtures as described above must be relatively dilute and require some form of intermixing. If the amount of water is reduced, the fat tends to form a very viscous continuous phase between the particles of ground bean, and this will prevent adequate oxidation.

It would be desirable to devise a process of enzymically oxidizing fats and/or fatty acids and that can be performed easily and to give high yields of the desired products. It would also be desirable to provide novel apparatus suitable for such processes.

SUMMARY OF THE INVENTION

According to the present invention, there is now provided a process for enzymic oxidation of a fatty acid in the presence of water and oxygen to produce an oxidation product characterized in that the fatty acid, water, and an enzyme for the oxidation are substantially uniformly distributed throughout a porous bed of solid support material in the substantial absence of a continuous liquid phase; oxygen is passed through the porous bed, and the oxidation product is recovered from the porous bed. The oxidation product may undergo further reaction.

BRIEF DESCRIPTION OF THE DRAWINGS

Suitable apparatus is described with reference to the accompanying drawings in which.

DETAILED DESCRIPTION OF THE PREFERRED EMBODIMENT

Figure 1:
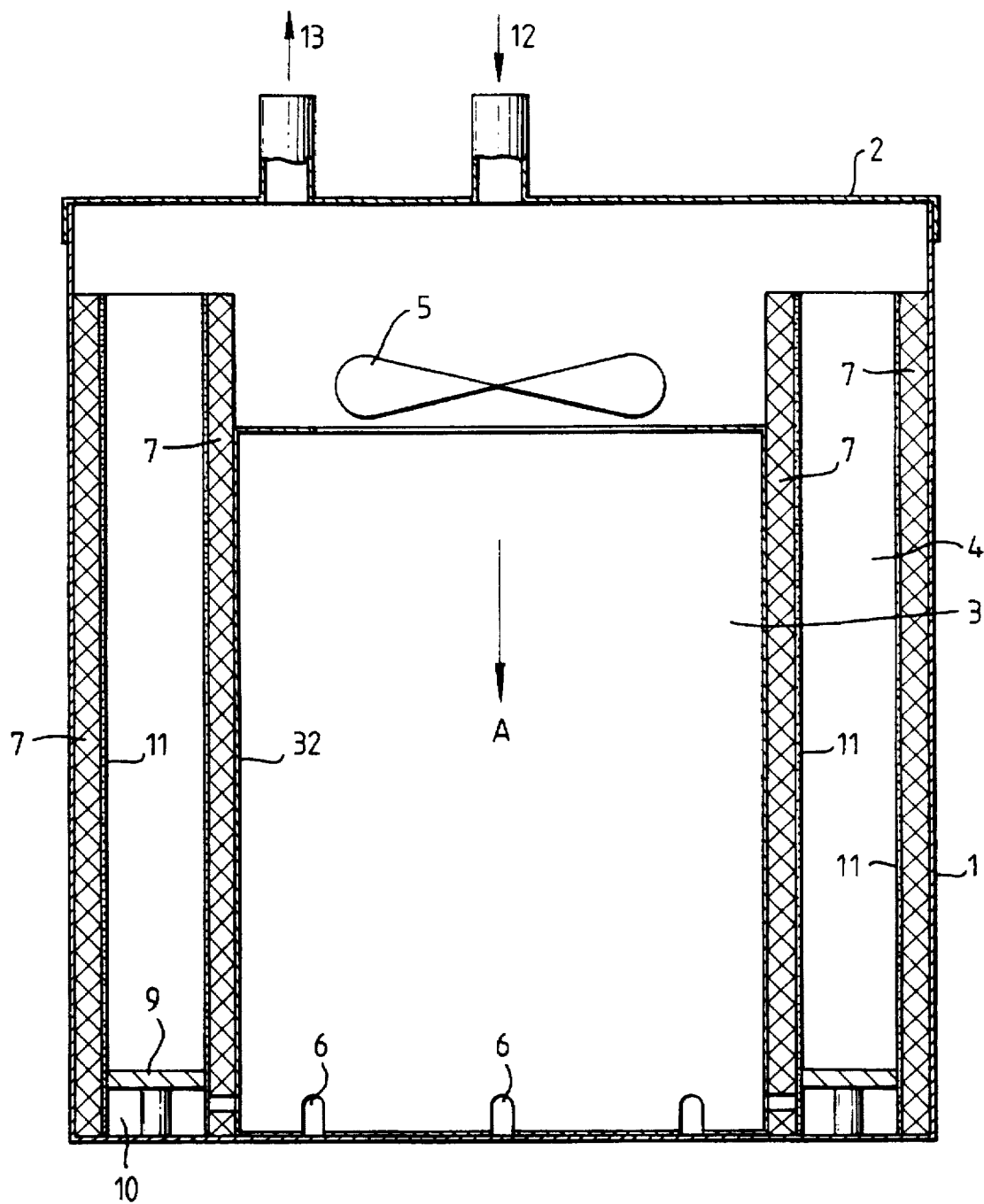
FIG. 1 shows a cross-sectional view of one apparatus.

The starting material is a fatty substrate which can be fatty acid alone, or mixed with fat or other ester, or fat alone (which is hydrolysed to acid prior to the oxidation process).

The fatty acids used by be saturated or unsaturated hydrocarbon fatty acids, or may be saturated or unsaturated hydroxy carboxylic acids.

Saturated fatty acids are oxidized in the beta position and will subsequently undergo decarboxylation. Unsaturated fatty acids undergo oxidative cleavage to give products having carbonyl groups at the point of cleavage. These aldehydes or ketones may undergo subsequent reduction to the corresponding alcohols. Decarboxylation of the oxidation products of saturated fatty acids is usually spontaneous due to the thermodynamically unstable nature of the oxidized compounds, but may result from a further enzymic reaction. Saturated, unsaturated, and hydroxylated fatty acids react to produce methyl ketones, aldehydes, and lactones, respectively.

Secondary alcohols can be produced as the final end product by reduction of product methyl ketones or primary alcohols from aldehydes: for example, if a reductase enzyme is present.

Unsaturated aldehydes and alcohols can be produced from doubly or polyunsaturated higher fatty acids such as linoleic or linolenic acid. Oxidative attack at one of the unsaturated groups breaks the double bond to produce, for instance, two fragments, each terminating with a carbonyl group. Particularly useful products of this type of reaction are hexenals and hexenols. For example, linseed oil contains doubly and triply unsaturated $C_{18}$ glycerides which result in the formation of unsaturated fragments, giving rise to hexenals and hexenols.

The invention is of particular value for the production of methyl ketones from saturated fatty acids.

A vital feature of the invention is that the oxidation is conducted on a support that is porous throughout the reaction, since this permits easy aeration and contact of substantially all parts of the material with oxygen. To maintain this condition, the support cannot be oil-logged or in the form of an aqueous suspension or slurry, and so this is in contrast to U.S. Pat. No. 4,769,243, which uses an aqueous slurry.

Since the liquid phase is carried on the porous bed of solid support, its aeration is controlled by the porosity of the bed. The concentration of the fatty acid in relation to the aqueous phase can be relatively high, and so the yield of product from the process is maximized. It would be difficult to obtain satisfactory aeration of a bulk liquid phase of the same concentration because of its physical properties. For instance, the maximum yield obtainable by a conventional liquid phase process would be around 15% or less, but in the invention it is possible easily to obtain yields of above 20%, and much higher if optimum conditions are selected.

The process has an additional advantage in that since it is a bio-process, as long as the starting products are of natural origin and not artificially produced, the products of the process can be classified as natural products.

The support is a porous matrix which may be fibrous (for instance an open web of fibers), but is preferably particulate. The particles may be non-porous, but preferably they are a porous particulate substance so that the surface area of the support is maximized. The bed can then be regarded as both macroporous (due to the interstices between particles) and microporous (due to porosity within particles). The particle size is generally from 0.001 to 5 millimeters, preferably from 0.01 to 2 millimeters. Examples of suitable support materials are inert, non-carbohydrate materials that may be inorganic or organic (generally synthetic polymeric) materials such as vermiculite and fibers or foams which may be made of plastic materials. Preferably the support is a carbohydrate, preferably a cellulose such as cellulose powder, rice flour, maize starch, wheat flour, woodpulp, or other carbohydrate porous matrices fibers or other particulate materials.

In the invention there must be substantially no continuous aqueous or other liquid phase. When a particulate material is used, the support preferably remains substantially friable throughout most (and preferably all) the process. Although some aggregation of particles is acceptable, the individual particles or aggregates of them should remain substantially separate from one another in order that porosity and aerobic conditions prevail substantially throughout the bed.

The enzymes may be pre-formed, or may be grown in situ. They must be suitable to induce the desired oxidative reaction of fatty acids. Pre-formed enzymes can be obtained from any suitable source, and should be mixed substantially uniformly throughout the carbohydrate or non-carbohydrate bed. The pre-formed enzyme may be obtained from a plant source, or may be of microbial origin. Examples are ground germinating soy beans in aqueous suspension or enzymes isolated from them, or alcohol oxidase from *Pichia pastoris*, or alcohol dehydrogenase from Baker's yeast.

Preferably, however, the enzymes are generated in situ, for example, by growth in the porous support of micro-organisms capable of producing the desired enzymes for effecting the desired conversion. This is of particular value when the fatty acid is part of a fatty substrate during the process which comprises both a fat and a fatty acid derived from the fat. The micro-organism should be distributed uniformly throughout the bed, as otherwise a proportion of the fatty substrate will not be exposed to the aerobic biotransformation. This uniform distribution can be achieved by for instance absorbing it into the particles while it is carried in, for instance, an aqueous nutrient medium. It is particularly preferred to use a filamentous micro-organism since then the growth of the micro-organism on the support results in the growth of filaments which carry the micro-organism to other parts of the bed. The micro-organism can be any of the molds that grow naturally on the fatty substrate or can be any other micro-organism capable of effecting the enzymic biotransformation of the fatty acid. When the micro-organism is being grown in situ, and especially when filamentous, the support is preferably unstirred during the process. The porous bed itself may move (e.g., on a conveyor), but the relative movement within the bed should be kept to a minimum.

An important feature is that when the enzyme is produced in situ, a limited source of carbohydrate for growth of the enzyme-producing micro-organism should be present throughout the bed. This source may be a soluble carbohydrate such as dextrins, glucose, or various monosaccharides. It may be added to a non-carbohydrate support, but preferably it is released from an otherwise insoluble carbohydrate support that may, for instance, be contaminated with for instance 0.1 to 5%, often about 1%, soluble carbohydrate before use. The preferred carbohydrates listed above generally provide a suitable source as well as being suitable supports.

It is generally desirable that the support material releases or otherwise provides part of the source of carbohydrate available to the micro-organism during at least most of the process, especially when the support is static and the micro-organism filamentous. Generally, the fatty substrate also serves as a source of carbon. However, in some instances it can be desirable to include a small amount of soluble saccharide, such as sucrose or glucose, in the aqueous medium to promote initiation of the process. If soluble saccharide is included after the process has been initiated, the product yield is liable to drop, possibly because the micro-organism is metabolizing the soluble saccharide in preference to the fatty product and the insoluble carbohydrate.

A mold that will provide the desired enzyme is preferably mixed into the support as spores which germinate on the support to form mycelia. Alternatively, mycelia may be added to the support; but this is generally not preferred, as mycelia are much less robust than mold spores and are liable to be damaged during distribution throughout the support. Growth conditions should be carefully regulated during the germination stage to obtain optimum results as the micro-organism is very sensitive to adverse conditions during this stage.

The germination stage produces mycelia which generally takes from around 1 to 6 days, and the optimum temperatures for this stage are ambient: for example, 15 to 30° C. preferably 18 to 25° C. In addition, the germination stage is sensitive to acidity, and although it has been found that free fatty acids can be added to the support bed for enzymic oxidation, the smaller chain fatty acids have been found to tend to prevent or impair the rate of germination. Accordingly, germination should preferably be conducted in the substantial absence of fatty acids of less than 8 carbon atoms. During this initiation phase, little or no oxidation of fatty acid takes place.

When germination is conducted in the presence of fatty acids, germination is followed by a lipolysis stage in which fat is hydrolysed to the fatty acid components.

The micro-organism then induces oxidation of fatty acid and this can cause a rise in temperature typically from ambient to between 35° to 50° C.

In order to limit excessive temperature rise, a cooling means may be used, and this is preferably a cooling coil and/or jacket. The temperature in the bed is generally below 50° C., preferably below 40° C., and most preferably below 35° C., throughout the reaction.

The fatty acid may all be pre-formed by any natural process (and the fatty substrate will then consist solely of fatty acid), especially when pre-formed enzyme is used. When the fatty acid is pre-formed, preferably it is added to the support bed gradually, as conversion occurs, because if the acid content in the bed is too high, the enzyme action may be affected. This is a particular problem with short chain fatty acids, and the problem can be minimized by using only fatty acids having a carbon chain length of ten or above. Preferably, some or all of the fatty acid is generated by hydrolysis in situ of a corresponding ester (for example an ethyl or other alkyl ester, but preferably a glyceride) either by a hydrolyzing enzyme produced by micro-organism grown on the support, or with the addition of some pre-formed lipase to effect the initial hydrolysis of fat or oil to fatty acid. In situ production of fatty acid is advantageous in that it gives a means of controlled release of fatty acid to the support bed and acts as a rate-limiting step in the process. The fatty substrate during the process will then contain both fatty acid and fat, but at the start of the process (i.e., before the lipolysis) may consist solely of fat.

Preferably the process comprises introducing the fatty acid as a fat (which may be a solid fat or an oil) and growing a micro-organism that provides both a lipase for hydrolysis of the fat and an oxidase for oxidation of the resultant fatty acid to ketone or aldehyde.

It is often preferred for some of the fatty acid to be produced from a fat or oil in situ and some of the fatty acid to be added to the reaction mixture, since this can increase yield. The fatty substrate can then comprise different types of fatty acids, and generally also fat. When the fatty acid is added to the support bed after the germination stage, it is distributed into the support bed in order to produce a substantially even distribution throughout the bed while aiming for the minimum disturbance of the bed. For instance, the fatty acid can be blended with separate porous support material, and this can then be blended with the bed containing the germinating micro-organisms since this reduces the amount of stirring needed to obtain uniform distribution.

A separate, first lipolysis stage may be provided in a separate reactor in which fat and lipase enzymes such as Candida lipase are reacted to produce fatty acid which is subsequently added to the bed. Preferably the subsequent addition of fatty acid to the bed is regulated.

Preferably, the fat used is coconut oil, but other suitable fats or oils include castor oil, linseed oil, arachis oil, sunflower oil, maize oil, palm leaf oil, palm kernel oil, or any edible oil. The amount of fatty substrate added as fatty acid and the amount added as fat can vary considerably. The source of fatty acid may comprise 100% fat or it may comprise 100% pre-formed fatty acid. However, in the preferred process where the hydrolyzing enzyme is formed in situ, the ratio of fat to fatty acid is generally between 1:10 and 50:1, and preferably from 1:5 to 10:1 by weight.

Particularly preferred fatty acids are those which occur naturally (as glycerides), and the preferred fatty acids are $C_{6-18}$ aliphatic carboxylic acids which may be saturated or unsaturated and may have one or more hydroxy groups.

In the case when the micro-organism is also the source of lipase and oxidase, and the fat used is, for example, coconut fat, the fatty acid preferably has a carbon chain length less than $C_{16}$, and most preferably less than $C_{14}$, because these lower carbon chain lengths appear to be preferentially oxidized by the micro-organisms. However, using other fat sources and/or other micro-organisms, preferred fatty acids may differ. We hypothesize that the reason for this is that initial fat hydrolysis is an extracellular reaction resulting from the lipase enzymes which are secreted by the micro-organism and act outside the cells to produce fatty acids, and the resultant fatty acids must be capable of migration into the cells of the microorganism through the cell wall, for the subsequent oxidation and decarboxylation, which is an intracellular reaction.

Suitable micro-organisms for producing enzyme or enzymes for hydrolyzing and oxidizing oils, fats, and fatty acids such as those discussed above, are molds from the Phycomycetes class, or the Ascomycetes or *Fungi imperfecti* classes. Preferably, those used are food grade molds such as *Penicillium roqueforti, Penicillium cameberti, Aspergillus niger, Aspergillus oryzae, Rhizopus japonicus,* or *Rhizopus oryzae*. Non-food grade molds are also suitable for the biotransformation, and examples are *Penicillium cyclopium* and *Eurotium herbariorum*. They conveniently can give methyl ketones.

Enzymes that are particularly suitable for converting linseed oil and similar polyunsaturated materials can be provided by any green leaf plant. Grass or germinating soya beans are examples of preferred materials because they have a relatively high content of the enzyme.

Octenols and hexenols can be obtained from germinating soya beans with unsaturated fatty oils such as linseed oil.

Castor oil and carotenoids may also be used as substrates in conjunction with grass, since this vegetation provides suitable enzymes.

For preparation of the support bed, the fatty substrate (which may be a solid or an oil at ambient temperature) may be warmed to assist loading by ensuring that the viscosity is low so that it will mix easily onto the support. Preferably, it is mixed with the particulate material before addition to the vessel in which fermentation is to occur. The mixing can be achieved using a mixing machine: for example, a Nauta or Winkworth mixer. Water or aqueous nutrient is also loaded onto the support in this way and may be added either prior to or following the addition of the fatty substrate.

Alternatively, the fatty substrate and water or aqueous nutrient may be mixed to form an initial emulsion which is then loaded onto the support. It may be necessary to add a suitable emulsifier to maintain the emulsion until it is loaded onto the particulate material to ensure that both components are distributed substantially evenly throughout the support. Suitable emulsifiers are, for example, lecithin, casein, and quillaja. Artificially produced emulsifiers may also be effective, but are less preferable for production of food grade products.

When the enzyme is pre-formed, either fat or fatty acid can be loaded onto the support. However, when the enzyme is produced in situ by the micro-organism, it is important to select the optimum conditions for enzyme induction in order to maximize growth and bioconversion. As explained above, due to the sensitivity of the germination stage, it is generally essential that the acid present should be at a relatively low concentration, and in particular there should be substantially no free fatty acid present having a short carbon chain length. It has been found that while the short chain fatty acids, for example $C_8$, are damaging or retarding to the germination stage, a $C_{10}$ fatty acid may be present and the germination can still take place.

When the germination stage is substantially complete, pre-formed fatty acids can be added directly to the support. These are generally $C_6$–$C_{18}$, and preferably $C_8$ and/or $C_{10}$ fatty acids. Preferably the fatty acids are added as a mixture of different carbon chain length fatty acids, such as occurs naturally. The acids can be added as, for instance, alkali metal salts.

The weight ratio of fatty substrate to water on the support should be carefully controlled for optimum yields, and is generally from 1:10 to 7:10, preferably from 1:3 to 4:7; and most preferably around 2:3. If there is too much fatty substrate, a fatty layer tends to separate out into the bottom of the reaction vessel and the process loses efficiency. If the amount of water is too high, the yield is reduced and there is a tendency for the bed to become saturated with water if the amount of fluid is increased to compensate for the low yield.

When the enzyme is formed in situ and a fatty acid is added to the support bed prior to germination, the substrate is preferably added at a concentration of from 2% to 30%, and most preferably the concentration is from 5% to 10%, based on the total weight of loaded support bed.

Where the fatty acid is added to the support bed after germination of an enzyme-producing mold, it is again generally added at a concentration of from 2% to 30%, and preferably 5% to 15%.

Concentrations of fatty acid below 2% can be used, but tend to be impractical, while the upper limit of fatty substrate that can be used is generally imposed by the possible loading of fatty substrate and water onto the support material and the moisture requirement of the micro-organism for effective growth.

In choosing suitable support materials, it should be noted that the micro-organism can affect the capacity of the support for the aqueous phase. For example, it has been found that for a particular fatty substrate-to- water ratio, the tendency for separation of the two phases is increased following inoculation of micro-organism into the bed of support material and its consequent rise in temperature.

In addition, the ratio of water to the support material and fatty substrate to the support should be controlled. Although it is desirable to have a high content of liquid phase, the support bed should not be fully saturated to the point where it will tend to form a continuous phase and reduce the passage of oxygen so that some parts of the support bed will, at least in part, no longer be aerobic.

The ratio of water to the support material is generally from 1:10 to 6:3, preferably from 1:3 to 5:3, and most preferably around 4:3.

It is naturally desirable that the load of fatty substrate and aqueous nutrient solution, or water, be as high as practicable without saturating the support and destroying its porosity. Generally, the total amount of fatty substrate and the aqueous nutrient solution or water that is absorbed into the support is from 15% to 99%, often 50% to 90%, by weight of the amount required to cause complete saturation as indicated by the formation of a substantially continuous phase. For instance, when as is often preferred, the support medium can absorb around 2 to 3 parts solution and fatty substrate per part support material, it is often convenient to absorb into the particles 0.7 to 1.3 (often around 1) part fatty substrate and 0.7 to 1.5 (often around 1.3) aqueous nutrient solution or water per part by weight support.

All the above ratios are optimum for a support bed of cellulose powder. However, they are also suitable for most supports, although some may required slightly different amounts for optimum results.

Where the enzyme is produced in situ, an appropriate nutrient source must be included: for instance, to ensure that all of the standard essential trace elements of biotransformation are available. Some essential elements will already be available as inevitable trace elements in, for example, the support material. Examples of essential elements are iron, copper, manganese, molybdenum, and selenium. The nutrient source is preferably included in the water that is loaded onto the support, in order to promote growth of the enzyme-producing micro-organism. Thus, the nutrient source and water are preferably an aqueous solution that provides adequate inorganic nutrients for the biotransformation, but typically can be Czapek type medium (often at 1.5 to 2.5, preferably about 2, times the normal concentration). Thus, the aqueous solution typically contains nutrients such as sodium, magnesium, potassium, zinc, copper, and iron; and generally contains 1.5 to 6 (preferably 3 to 5) g/l sodium nitrate, 0.3 to 2 (preferably about 0.8 to 1.2) g/l magnesium sulphate heptahydrate, 0.5 to 2 (preferably about 0.8 to 1.2) g/l potassium chloride, and trace quantities of ferrous sulphate, zinc sulphate, and copper sulphate.

It is naturally important that there should be no extraneous poisoning contamination present in the porous bed. It is a recognized problem in many microbiological processes that some contaminants may interfere with or stop desired microbiological processes at certain concentrations, and so the materials and conditions used in the invention should not be such as to produce contamination by toxic concentrations of potentially toxic materials. For instance, if a toxic impurity might be leached from apparatus used in the process by contact with an acidic medium, contact between fatty acid and that apparatus should be avoided.

The aqueous medium may be buffered to a pH at which the process proceeds most efficiently. Although the process can be performed at pH values in the rage of, for instance, 4 to 8, best results are generally achieved when the pH is in the range of 6 to 7.5, and most preferably when it is buffered with phosphate to a pH of about 6.8. However, as discussed above, fatty acids such as $C_{10}$ may be added to the support bed after the initial germination, and in these cases the pH will be lower.

The desired product formed during the process may escape from the porous support bed as it is produced and thus can be collected from gas escaping from the bed during the process. However, this may be unnecessary since the amount of product evolved as vapor may be very low, and the bulk of the product may be trapped in or on the support and the bed that it forms; and the desired products can be recovered from the bed at the end of the process. The trapping can be either by absorption into any porous particles in the support, or by dissolution or adsorption with the organic materials (especially mycelium) therein, or both. It is particularly surprising and convenient that the process can be substantially run to completion before recovering the products from the support bed.

Recovery of the product of the bioconversion can be achieved by distillation, preferably by mixing the contents of the bed in water, distilling the mixture, and recovery of the distillate.

The collected product is a mixture containing natural components, and this mixture itself can be very useful. For example, the product from coconut oil is a mixture containing natural ketones having excellent blue cheese flavor properties. However, the individual components of the product mixture are particularly useful; and these can be obtained from the mixture by a normal procedure of fractional distillation, preferably under vacuum.

The process may be carried out in a biotransformation vessel which contains the support bed and that includes means for aerating the bed so as to ensure sufficient oxygen is available for the required oxidative process at substantially all positions in the bed.

The process generally may be carried out in a semi-continuous or continuous process (for example on a conveyor), but is preferably conducted batch-wise.

It is generally desirable for the bed to be static and unstirred, since stirring the support bed may tend to help form a continuous liquid phase which will reduce porosity and may prevent air permeation through the bed, in addition to causing damage to mycelia.

Generally, the bed is less than 2 meters (preferably less than 1 meter) deep since increasing the depth of the bed increases the pressure in the bed and the risk that the friable mixture will compress and tend towards a continuous phase. Generally the-bed is greater than 0.1, and preferably greater than 0.5, meters deep.

Air or oxygen should be passed through the support bed at a rate sufficient to stimulate rapid biotransformation, but insufficient to fluidize the bed. A satisfactory rate is 0.25 to 5 liters of air per minute, and more preferably 1 to 3 liters of air per minute, per 1000 kilograms of the loaded support bed.

It is often preferred that the concentration of oxygen in the gas supply should be below the oxygen content of air since better results are obtained using a high volume of a dilute gas than with a low volume of a concentrated gas, because it is easier to control the actual amount of oxygen delivered to each part of the bed. Preferably the gas contains 1% to 10% oxygen, often 2% to 5%, with the balance being inert gas such as nitrogen.

One way of achieving this dilute oxygen is by recycling the oxygenating gas within a loop consisting of a bio-reactor or including one or more reactors, and adding sufficient oxygen or air to the recycle to maintain the desired concentration. The recycle will have a high content of carbon dioxide; and we have surprisingly found that this does not interfere with the process, and that the carbon dioxide is an inert gas in this process. Accordingly, a preferred gas is 1% to 10% (often 1% to 5%) oxygen, above 50% $CO_2$, and 0% to 49% nitrogen. The amount of $CO_2$ is often 70% to 90%.

When recycling, it is necessary to prevent escape of too much water from its desired location and, in particular, it is necessary to ensure water does not condense in the recycle and cause localized waterlogging of a bed.

The biotransformation vessel is preferably supplied with a gas inlet and with an outlet. Both connections may be fitted with filter units, scrubbers, or valves in order to prevent microbial contamination.

One way to ensure substantially even distribution throughout the biotransformation vessel is to force gas up through the bed from a distribution manifold across the base of the bed.

If the vessel is a substantially airtight cylindrical or other vessel having a removable lid, then it can be convenient to have a flexible gas supply duct leading down through the lid and support bed to below the manifold. A gas outlet is generally provided towards the top of the vessel so that waste or product gases can be removed. Simple apparatus of this type can be a substantially cylindrical vessel with a capacity of approximately 50 to 450 liters, and most preferably from 180 to 340 liters.

Instead of passing the oxygenating gas upwards, it is often preferred to pass it laterally through the bed from a series of spaced-apart gas supply passages that each supplies gas into the bed over substantially its entire length. The extent of permeation will depend on the material of which the bed is formed. It can be determined by simple experiment, but is generally not more than about 10 cm and is often 5 to 8 cm. Thus, the separation between two passages should be not more than about 20 cm, often not more than 10 to 16 cm. This technique has the advantage of providing more uniform oxygen concentration than by upflow from a manifold.

Preferred apparatus for use in the invention is novel and can be used for a variety of fermentations conducted using a porous bed (such as citric acid production) or for the fermentations of the invention. It comprises a sealable bio-reactor that can contain the porous bed; a gas inlet for supplying oxygenating gas to the reactor; a gas outlet; passage means defining a plurality of passages that 6an open along their length into the bed and that communicate with the inlet and that are preferably spaced 5 to 20 cm (preferably 5 to 15 cm) apart; and means for forcing oxygenating gas through the inlet and along and out from the passages and into the bed.

The invention includes both the empty vessel and the vessel filled with the bed. The passage means can be horizontal and spaced apart both horizontally and vertically, but preferably they are substantially vertical.

The spacing of the passage means relative to one another is dependent upon the porosity of the bed, and this is largely dependent upon the particle size of the support material forming the bed. The passage means are spaced so that gases can permeate to substantially all areas of the bed.

One suitable passage means comprises a plurality of rod shaped passages that provide outer annular gas passages. For instance, each passage can be defined by a permeable tube, allowing gas to escape along its length, preferably at a substantially uniform rate along the length. However, the annular passages can also be formed by forcing tubes through the bed so as to create an annular layer around each tube that is of lower density than the rest of the bed. For instance, each tube can be inserted while covered by a sheath, and the sheath can then be removed. To prevent blockage of the tube during insertion, the tube can have a removable core which can be removed after insertion so that air can then flow down the center of the tube, out at the lower end, and up through the low density annulus around the rod. Additionally, low density annulus may be formed by shrinkage of the bed away from the tube during use.

Another suitable passage means comprises a substantially self-supporting open network that preferably extends up through the bed and that communicates at its base with the inlet. Gas is forced from the inlet into the base of the network and flows up the network and out into the bed from most or all of the surface area of the network. Preferably the networks are substantially parallel to one another and not more than about 10 to 15 or 20 cm apart. Generally, two networks define the sides of an annular bed.

In order to maintain the desired humidity in the bed, there is preferably a trough in the base of the bed in which water can collect when in use, and a wicking layer of fabric extends up from this trough over part or all of some or all of the networks, so as to promote evaporation of water into the gas surrounding the networks and into the bed. The evaporation also helps maintain a uniform cool temperature throughout the bed.

The process of the invention can also be conducted using flat trays carrying a shallow layer of support or a drum method as described in *Advances in Applied Microbiology*, volume 28 (1982), "Solid Substrate Fermentations," by K. E. Aidoo, R. Hendry and B. J. Wood, page 209.

The apparatus in FIG. 1 comprises an air-tight vessel (1) having a sealable closure (2) and an inner body (3) defined by cylindrical walls (32) extending upwards through the vessel, but which does not extend fully to the top of the vessel. This defines an annular space (4) inside the vessel. A fan (5) is positioned at the top of the inner body (3) for circulating the gases in the vessel down through air ways (6) cut in the walls (32) of the inner body around its base and leading into the annular chamber (4). A bed of porous support material on which the fermentation takes place is positioned in the annular space (4). Gas inlet (12) is used to provide oxygen and any other required gases to the apparatus, and outlet (13) is used for removal of exhaust gases.

A gas permeable open network (7) is provided around the inner and outer walls of the annular space. The network is provided by an open mesh of substantially rigid, self-supporting material which extends from the bottom of the vessel upwards towards the top of the vessel.

As heat is produced during biofermentation, water evaporates off the bed and is liable to condense on the sides of the vessel and run down into the base of the vessel. Therefore, in order to prevent water-logging of the bottom portion of the support bed, an annular raised platform (9) is provided in the annular space and above air ways (6) so that a trough or chamber (10) is provided beneath the bed for collection of condensed water and circulation of gases. In addition, in order to provide redistribution of this condensed water to the support bed a second layer (11) is provided next to the mesh layer (7) inside the vessel around the annular walls and comprises a wicking material. The wicking layer (11) is positioned so that its lower edge reaches substantially to the bottom of the vessel into chamber (10) so that it is in contact with any collected condensed water. The wicking action of the layer then draws the condensed water back up the side of the vessel where it can be reabsorbed by the porous support bed either by evaporation or by conduction.

It has been found that, using the bed of porous support material described in the examples, adequate oxygen distribution is achieved for up to approximately 8 cm from the edge of the bed. Therefore, in order to achieve effective oxygen distribution throughout the porous bed, the distance between the gas permeable layers (7) should be no greater than 16 cm. This distance may vary with porosity of the support bed.

The apparatus may be arranged in other ways: for example, a series of concentric annuli may be provided for containing the support bed, each annulus separated from the next by a gas permeable layer (optionally with a wicking layer).

Figure 2:
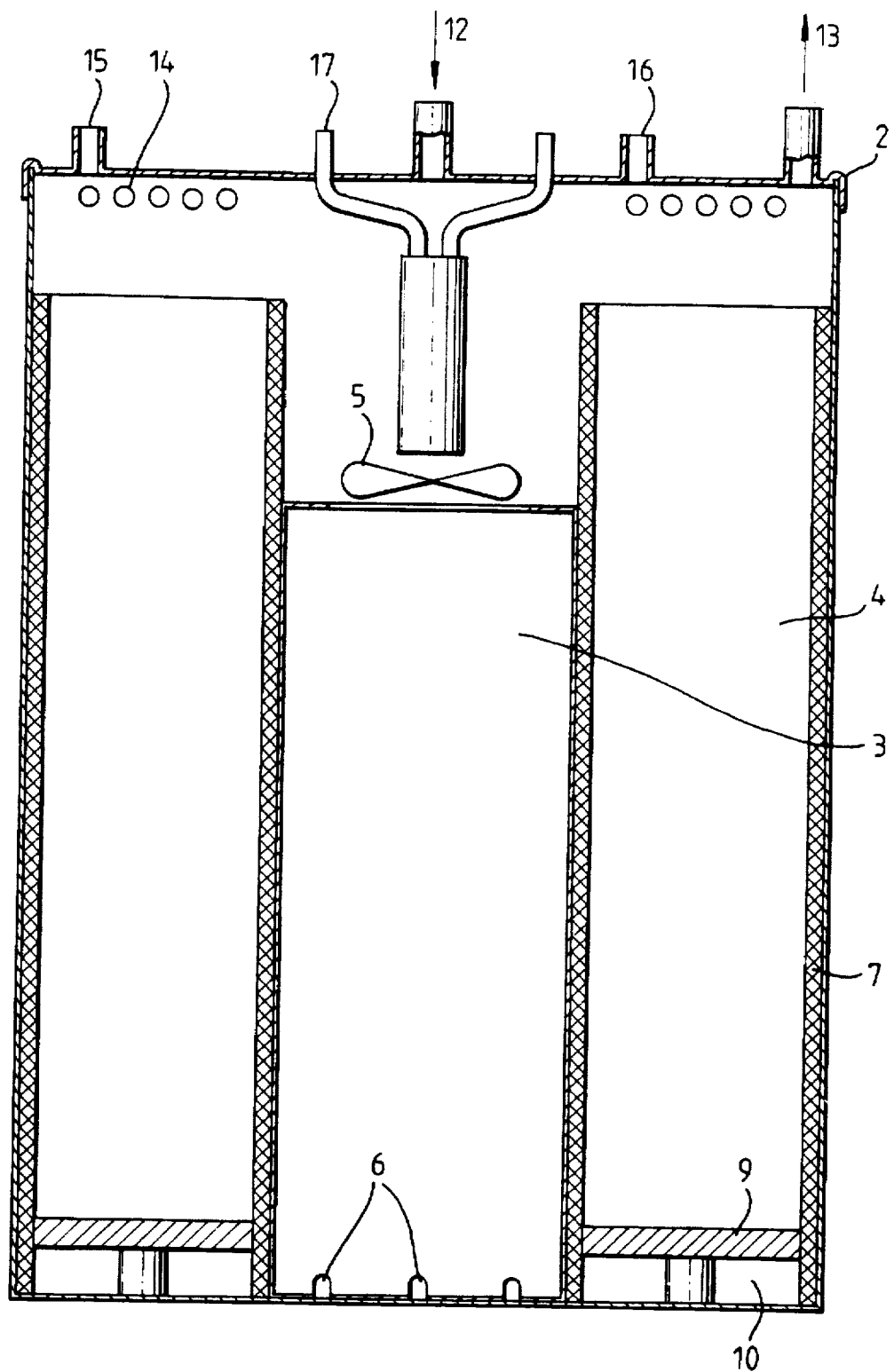
FIG. 2 illustrates a cross-sectional view of a second apparatus.

FIG. 2 illustrates a similar apparatus except that the wicking layer is omitted and there are cooling coils (14). Cooling water enters the cooling coils via inlet (15) and leaves the cooling coils via exit (16). Evaporated water from the support bed condenses on these cooling coils and, because of their position above the annular space (4) for containing the porous bed of support material, condensed water falls back into the support bed and is redistributed. FIG. 2 also shows fluid drive (17) for the hydraulic powering of the fan (5).

The reactor may be any shape, but for convenience is preferably cylindrical. The inner body may be integral with the vessel or may be a separate body positioned in the bottom of the vessel. The apparatus can be made of any suitable material which will not interfere disadvantageously with the reaction inside the vessel, but preferably is prepared from a material which can be autoclaved for sterilization: for example, plastics such as polycarbonate plastic, polypropylene, or other suitable materials. The fan (5) may be powered by any suitable means, but is preferably powered by pneumatic or hydraulic means as this minimizes safety hazards.

The gas permeable network may be formed from any material which will not inhibit the reaction in the reactor, but is preferably made from autoclavable material. Generally, the gas permeable network is formed of, for example, plastics materials in which the diameter of the network strands is preferably sufficient to make the mesh self-supporting, but small enough to leave substantial spacing within the layer. For example, the strands may be from 0.5 to 5 mm thick, preferably from 1 to 2 mm thick, and preferably at least 50% of both the transverse and longitudinal cross-section areas of the layer comprises open pores in the network.

The wicking layer may be formed from any material which will provide a wicking action to redistribute the water: for example, an open wave cloth such as linen.

Figure 3:
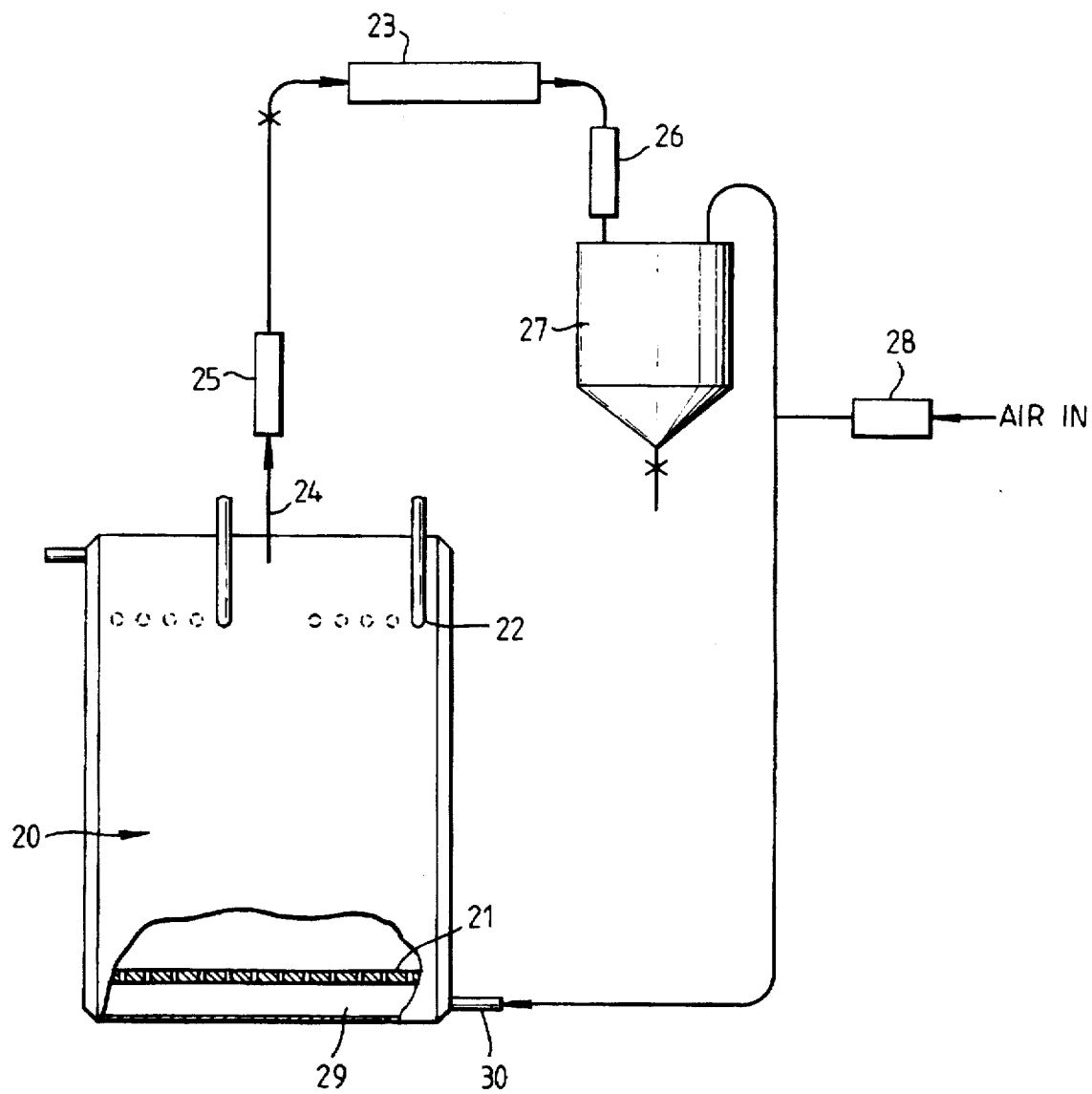
FIG. 3 is a diagrammatic representation of another apparatus that includes recycle.

FIG. 3 is a diagrammatic representation of an alternative reactor system. The reactor vessel (20) is a closed, substantially air-tight container having at its base a chamber (29) connected to the main body of the reactor by an air distribution plate (21). The reactor is also provided with cooling coils (22), an exhaust gas outlet at the top of the reactor, and a gas inlet (30) at the base of the reactor. The apparatus illustrated is a closed-loop circulation apparatus. Pump (23) draws gas out of gas outlet (24) and through condenser (25). The escaping gas can carry heat out of the bed. As a result, gas is drawn through gas inlet (30) and through air distribution plate (21). Instead of relying on vacuum to draw gas into the reactor, less preferably gas can be pumped into the vessel at a higher pressure.

The supply of available oxygen can be controlled by its addition to the circuit. This addition may be made either by sucking in oxygen into the negative pressure side, or by pumping oxygen in on the positive pressure side of the pump.

Gas can be recirculated through the apparatus so that the gases drawn into tee apparatus are drawn from the pump via the condenser (26) and reservoir (27) which will collect any condensed water. Monitors may be introduced into the circuit to detect the exact oxygen concentration.

The initial gas supply may enter the system via flow meter (28).

Figure 4:
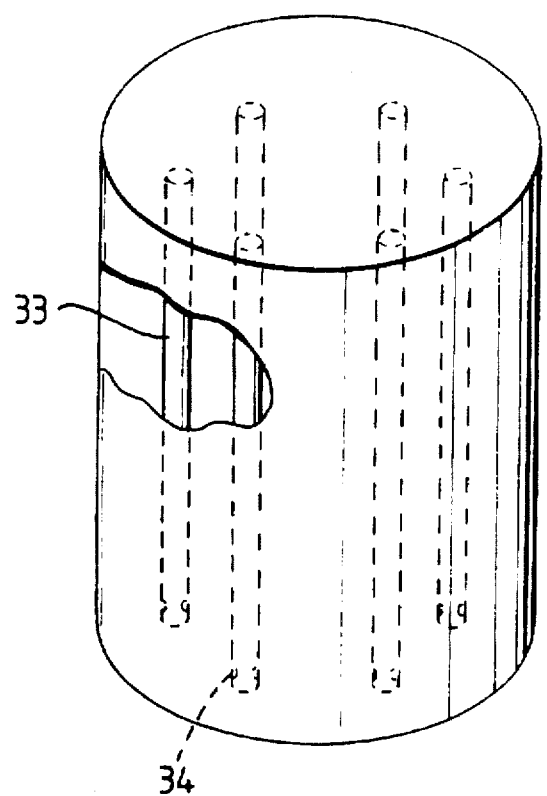
FIG. 4 shows a partially cut away perspective view of one arrangement of rod passage means in the bed-containing portion of an apparatus.

FIG. 4 represents a partially cut away perspective view of the portion of the apparatus that contains a cylindrical bed of support material having an arrangement of rod passage means for distributing gases throughout the bed. Gases are supplied from an upper manifold (not shown) to the top of each of hollow tube (33) and down the length of the tube. Gases then exit hollow tubes (33) through exit holes (34) at the bottom of each tube and pass up the length of the tube in an annular zone around each tube and that is substantially free of particulate material. Additional holes (34) can be distributed along the length of each tube, if required, to provide a more uniform gas supply along the length of each tube. The gas migrates laterally from around the tubes and into the porous bed. The spacing apart of hollow tubes (33) is such that gases can permeate substantially all areas of the bed. This is dependent upon the porosity of the bed and particle size of the support material. Exhaust gas leaves the support bed and exits from the apparatus via a gas outlet.

Figure 5:
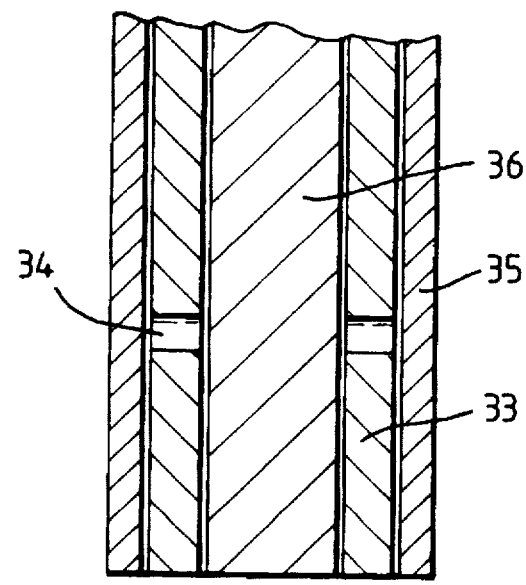
FIG. 5 shows a cross-sectional view of a rod with removable core and sheath in position before insertion into a bed.

FIG. 5 represents an enlarged cross-sectional view of the lower portion of a tube with removable core and removable sheath in position, in preparation for insertion into a bed. Tube (33) is provided with exit holes (34) at its end and along its length. A removable close-fitting sheath (35) is provided around hollow tube (33) and a removable close-fitting core (36) is provided inside hollow tube (33). This arrangement is inserted into a bed of porous support material and, once in place, the core (36) and sheath (35) are removed, leaving hollow tube (33) free of support bed material and with an empty annulus around the tube. Gases can then travel freely down the inside of the tube end and leave via exit holes to enter the empty annulus around the tube for travel along the outside of the tube and permeation into the bed.

EXAMPLE 1

45 kilograms of coconut oil were dispersed onto 45 kilograms of cellulose powder and mixed in a Nauta mixer. 60 kilograms of Czapek type medium were mixed into the cellulose powder and coconut oil mixture until an even texture was obtained. The Czapek type medium comprised sodium nitrate 4 g/l, magnesium sulphate 1 g/l, potassium chloride 1 g/l, ferrous sulphate 0.02 g/l, trace elements: zinc sulphate 0.01 g/l and copper sulphate 0.005 g/l, with 0.075 moles/l potassium phosphate buffer at pH 6.8.

The final mixture was discharged into a biotransformation vessel comprising an open-top drum having an air-tight lid and a flexible air inlet running through the mixture and to a manifold in the base of the drum and a gas outlet in the lid of the drum.

*Aspergillus niger* had been grown on malt Czapek agar at 25° C. The spores were harvested after approximately 10 to 14 days. Between $10^7$ and $10^9$ spores per kilogram of loaded support bed were used for inoculation. Air was pumped to the vessel at a rate of 3 liters of air per minute.

Germination of the spores occurred over the first 2 to 6 days, and the temperature rose from ambient temperatures to a maximum of 50° C. Elevated temperatures were maintained over the course of the fermentation, and as the fermentation came to an end after between 20 and 35 days, the temperature in the vessel began to fall gradually.

The methyl ketone products were separated from the fermentation mixture by water distillation. The density of the oily product was 0.82 grams/ml and the product separated out from the water and could easily be removed.

A portion of this product was fractionally distilled under vacuum using a column of twelve theoretical plates in order to obtain the individual methyl ketones. The total yield of methyl ketones was approximately 16%, based on the weight of coconut oil.

EXAMPLES 2 TO 4

Example 1 was repeated, but with the addition of capric and/or caprylic acid into the reactor after germination of the mold. The quantities of Czapek type medium, coconut oil, and oxygen were varied. The total yields of mixed ketones produced are shown in Table 1. The poor yields obtained for examples 2 and 4 were thought to be due to the effects of toxic trace elements.

TABLE 1

| | Example: | | |
|---|---|---|---|
| | 2 | 3 | 4 |
| Amount of coconut oil | 22.5 Kg | 3.00 Kg | 3.00 Kg |
| Amount of Czapek medium | 50.0 Kg | 6.65 Kg | 4.55 Kg |
| Amount of Cellulose powder | 37.5 Kg | 6.65 Kg | 4.55 Kg |
| Amount of capric acid | 15.0 Kg | 2.70 Kg | — |
| Amount of caprylic acid | — | — | 0.90 Kg |
| Total weight | 125.0 Kg | 19.00 Kg | 13.00 Kg |
| Rate of flow of air | 3 l min$^{-1}$ | 1 l min$^{-1}$ | 1 l min$^{-1}$ |
| Yield of mixed ketones (based on weight of fatty substrates) | 9% | 25% | 12% |
| Yield of nonan-2-one/ heptan-2-one (based on weight of capric/caprylic acid) | 17% | 46% | 25% |

EXAMPLE 5

3 kilograms of coconut oil were dispersed into 3.5 kilograms of cellulose powder using a Winkworth mixer. 3.5 kilograms of Czapek type medium were mixed into the cellulose powder and coconut oil mixture until an even texture was obtained (Czapek type medium as before). The final mixture was discharged into a biotransformation vessel as shown in FIG. 1.

*Aspergillus niger* produced as for Example 1 was inoculated into the biotransformation vessel. Air was pumped to the vessel at a rate of 1 liter of air per minute. Germination of the spores occurred over the first 4 days, at which time a separately prepared mixture was added. The separately prepared mixture comprised 1.5 kilograms of capric acid dispersed into 1.75 kilograms of cellulose powder, followed by 1.75 kilograms of Czapek type medium. This separately prepared mixture was added directly to the fermenting mixture in the biotransformation vessel and mixed together by stirring. The biotransformation vessel was resealed and the air flow continued at 1 liter of air per minute. Elevated temperatures were maintained over the course of the biotransformation, and the mixture was sampled after a total of 18 days fermentation.

The volatile products in the sample were isolated by water distillation, and the composition of the oily distillate was determined by gas chromatography.

After a total of 29 days fermentation, the process was stopped and a further sample taken for distillation and analysis of the oily distillate.

The coconut fat was found by analysis to contain 6.1% of capric acid, which gives 274.5 g of capric acid (as glycerides) in the coconut fat used for the experiment. In addition, 1500 g of capric acid was added to give a total of 1774.5 g of available capric acid in a total mass of 15 kilograms. This amount of captic acid is theoretically capable of conversion into 1466 g of nonanone. After 18 days fermentation, the total content of nonanone in the 15 kilograms of fermenting matrix was found to be 907 g, which was a 62% conversion; and after 29 days fermentation the content of nonanone was 1209 g, which was an 82% conversion. This example illustrates the improved yield obtained by carrying out the process in the novel apparatus of FIG. 1 and is due to improved control of temperature and aeration throughout the bed.

What is claimed is:

1. Apparatus for fermentation reactions comprising a sealable vessel that can contain a porous bed of solid support material, a gas inlet for supplying oxygenating gas to the vessel, a gas outlet, passage means comprising a network of a plurality of substantially parallel, spaced apart hollow tubes that can open along their length into the bed, extend through the bed, and that communicate with the inlet, means for creating an annular layer of support material around each tube that is of lower density than the rest of the bed, and means for forcing oxygenating gas through the inlet and along and out from passages and into the bed, whereby gas can flow through the annulus and out into the bed from most or all of the surface area of the network.

2. Apparatus for fermentation reactions comprising a sealable vessel that can contain a porous bed of solid support material, a gas inlet for supplying oxygenating gas to the vessel, a gas outlet, passage means comprising a plurality of substantially parallel, spaced apart, substantially self supporting open networks that extend up through the bed and that each communicate at its base with the inlet, and means for forcing oxygenating gas through the inlet and along and out from passages and into the bed, whereby gas can be forced from the inlet into the base of the network and flow up the network and out into the bed from most or all of the surface area of the network.

3. Apparatus for fermentation reactions comprising a sealable vessel that can contain a porous bed of solid support material, a gas inlet for supplying oxygenating gas to the vessel, a gas outlet, passage means comprising a plurality of substantially parallel passages spaced apart by a separation of 5 to 20 cm, that can open along their length into the bed and that communicate with the inlet, and means for forcing oxygenating gas through the inlet and along and out from passages and into the bed.

4. Apparatus according to claim 2 further comprising a trough in the base of the bed wherein water can collect in use, and a wicking layer of fabric extending up from the trough over part or all of some or all of the networks, so as to promote evaporation of water into the gas escaping from the networks into the bed.

* * * * *